(12) United States Patent
Hanson et al.

(10) Patent No.: US 9,638,660 B2
(45) Date of Patent: May 2, 2017

(54) TEST STRIP EJECTOR FOR MEDICAL DEVICE

(71) Applicant: Roche Diagnostics Operations, Inc., Indianapolis, IN (US)

(72) Inventors: James R. Hanson, Brownsburg, IN (US); Derek C. Lotarski, Noblesville, IN (US); Matthew C. Sauers, Indianapolis, IN (US); Anthony J. Uberta, III, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/183,986

(22) Filed: Feb. 19, 2014

(65) Prior Publication Data

US 2014/0166482 A1 Jun. 19, 2014

Related U.S. Application Data

(62) Division of application No. 13/538,023, filed on Jun. 29, 2012, now Pat. No. 8,715,571.

(51) Int. Cl.
*G01N 27/327* (2006.01)
*A61B 5/05* (2006.01)
*G01N 27/416* (2006.01)
*G01N 33/487* (2006.01)
*A61B 5/145* (2006.01)

(52) U.S. Cl.
CPC .......... *G01N 27/416* (2013.01); *A61B 5/145* (2013.01); *G01N 33/4875* (2013.01); *Y10T 436/11* (2015.01); *Y10T 436/112499* (2015.01)

(58) Field of Classification Search
CPC .................................................. G01N 33/4875
See application file for complete search history.

(56) References Cited

U.S. PATENT DOCUMENTS 4,302,420 A * 11/1981 Jakubowicz ......... G01N 21/474
356/244
6,189,370 B1 2/2001 Neel et al.
7,585,464 B2 9/2009 Amano et al.
(Continued)

FOREIGN PATENT DOCUMENTS

EP 1321769 A1 6/2003
EP 1382968 A1 1/2004
(Continued)

*Primary Examiner* — P. Kathryn Wright
(74) *Attorney, Agent, or Firm* — Harness, Dickey

(57) ABSTRACT

A system and method for receiving and ejecting a test strip of a fluid testing device. The system includes parallel first and second guide rails defining a rail cavity between the guide rails. A sled includes a sled post and opposed first and second side leg sets each having at least one deflectable leg. Each of the deflectable legs is externally slidably engaged to one of the guide rails limiting the sled to only sliding motion in either a loading direction or an opposite ejection direction. An actuator arm is rotatably connected to a mechanism assembly. The sled post is received in an actuator arm slot. Actuator arm rotation in a loading rotational direction displaces the sled in the loading direction in a sliding motion. Subsequent opposite rotation of the actuator arm in an ejection rotational direction displaces the sled in the ejection direction and ejects the test strip.

9 Claims, 12 Drawing Sheets

(56) References Cited

U.S. PATENT DOCUMENTS

| | | |
|---|---|---|
| 7,819,283 B2 | 10/2010 | Chambers et al. |
| 8,057,753 B2 | 11/2011 | DeAngeli et al. |
| 2005/0224345 A1 | 10/2005 | Taniike et al. |
| 2007/0255114 A1 | 11/2007 | Ackermann et al. |
| 2008/0229808 A1 | 9/2008 | Lee |
| 2009/0108013 A1 | 4/2009 | Van Der Velde et al. |
| 2009/0227854 A1 | 9/2009 | Ohama et al. |
| 2010/0012530 A1 | 1/2010 | Watanabe et al. |
| 2010/0319170 A1* | 12/2010 | Hsu .................... G01N 33/4875 24/457 |
| 2011/0040160 A1 | 2/2011 | Sakata et al. |
| 2011/0143562 A1 | 6/2011 | Wu et al. |
| 2011/0186588 A1 | 8/2011 | DeAngeli et al. |
| 2012/0143085 A1 | 6/2012 | Sauers et al. |

FOREIGN PATENT DOCUMENTS

| | | |
|---|---|---|
| EP | 1480037 A1 | 11/2004 |
| EP | 1762848 A1 | 3/2007 |
| EP | 1983339 A1 | 10/2008 |
| EP | 2071326 A1 | 6/2009 |
| JP | 2003114213 A | 4/2003 |
| JP | 2004101514 A | 4/2004 |
| WO | WO-0208753 A2 | 1/2002 |
| WO | WO-2004/063747 A1 | 7/2004 |
| WO | WO-2005/080966 A1 | 9/2005 |
| WO | WO-2006066123 A1 | 6/2006 |
| WO | WO-2007/083773 A1 | 7/2007 |
| WO | WO-2008/016137 A1 | 2/2008 |
| WO | WO-2009/055643 A2 | 4/2009 |
| WO | WO-2010139864 A1 | 12/2010 |

\* cited by examiner

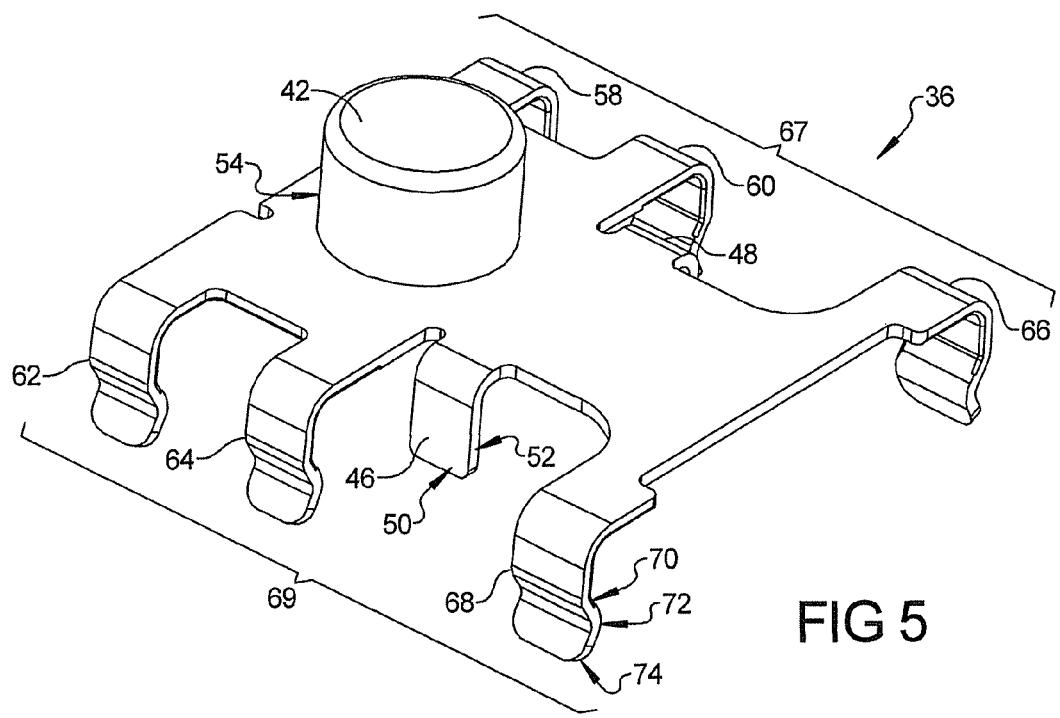

TEST STRIP EJECTOR FOR MEDICAL DEVICE

CROSS-REFERENCE TO RELATED APPLICATION

This application is a divisional of U.S. patent application Ser. No. 13/538,023 filed on Jun. 29, 2012 (allowed). The entire disclosure of the above application is incorporated herein by reference.

FIELD

The present disclosure relates to a system and method for measuring a sample such as a body fluid, and more particularly to a device and method for loading and then ejecting a sample containing test strip following measurement.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides for readout of the glucose level.

Known meters receive the test strip in an insertion direction that also engages the electrical strip conductors of the test strip with the electrical contacts of the meter. As the test strip is loaded by the user, the insertion motion is used to drive the electrical contacts of the test strip into engagement with the contacts of the meter. The strip ejection system permits ejection of the dosed test strip following testing without further contact of the test strip by the user. Any interference with or sliding contact of the electrical contacts of the test strip during insertion, however, can damage the electrical contacts or misalign one or more of the contacts. A force applied to eject the test strip of known strip ejection systems can also cause racking or rotation of the test strip which can bind the test strip or interfere with ejection.

For example, the measurement device of U.S. Published Patent Application No. 2010/0012530 to Watanabe et al. includes a pushing member 11 having projection part 11*b* that is slidably guided within a pushing member cover 12. Clearance between the projection part 11*b* and pushing member 12 therefore limits the control available to reduce deflection of pushing member 11 during its travel to displace a sensor 200. In addition, pushing member 11 includes a single substantially centrally positioned projection part 11*a* guided in a notch 10*a*. Control of racking of the pushing member 11 during travel is limited by the tolerances between the projection part 11*b* and pushing member cover 12, and between the projection part 11*a* and notch 10*a*. A braking system having a first braking part 13 in contact with a side wall of the sensor 200 is provided to slow down the exit speed of the sensor. This system does not preclude racking of either the pushing member 11 or the sensor 200, has only the single projection part 11*b* to contact and drive the sensor 200 which can therefore be off-center of the sensor 200, and adds the complexity of a braking system to limit ejection velocity.

European Patent Application EP 1321769 to Pugh appears to disclose a test strip dispensing system having strip push members 116, 210 guided between rails 100 or 214. Rails of this design are positioned external to the strip push members. The strip push members include outer wall areas such as ledges 220 acting as guides. Ledges 220, however, are positioned within the rails 214, therefore continuous positive contact between the strip push members 116, 210 and the rails to limit racking is not provided and racking can occur due to a tolerance between the components. The design of strip push members 116, 210 and rails 100, 214 also precludes installation in a direction perpendicular to the push member travel direction.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one embodiment of the disclosure, a test strip ejector system for receiving and ejecting a test strip of a fluid testing device includes first and second guide rails defining a rail cavity between the guide rails. A sled having first and second spatially separated contact faces is positioned in the rail cavity. The sled includes opposed first and second legs, each of the legs connected externally to and slidably coupled with respect to one of the first or second guide rails for sled motion in each of a loading direction and an ejection direction. An actuator arm is rotatably connected to the fluid testing device. The sled is coupled to the actuator arm such that rotation of the actuator arm in a loading rotational direction moves the sled in the loading direction to position the sled in a test strip test position. Opposite rotation of the actuator arm in an ejection rotational direction operates to displace the sled in the ejection direction away from the test strip test position and to position the first and second contact faces in direct contact with the test strip to eject the test strip from the fluid testing device.

In another embodiment, a test strip ejector system for receiving and ejecting a test strip of a fluid testing device includes parallel first and second guide rails defining a rail cavity between the guide rails and a sled having a sled post and opposed first and second legs. Each of the legs is connected externally to and slidably coupled with respect to one of the first or second guide rails thereby limiting displacement of the sled to only sliding motion in either a loading direction or an opposite ejection direction. The test strip is in direct contact with the sled during motion in at least the ejection direction motion. An actuator arm is rotatably connected to the fluid testing device. The sled post contacts the actuator arm such that sliding motion of the sled in the loading direction and rotation of the actuator arm in a loading rotational direction positions the sled in a test strip test position. Opposite rotation of the actuator arm in an ejection rotational direction operates to displace the sled in the ejection direction and to eject the test strip.

In a further embodiment, a method is provided for receiving and ejecting a test strip by a mechanism assembly of a fluid testing device. The mechanism assembly includes first and second guide rails in parallel alignment device creating a rail cavity between the guide rails, an actuator arm, and a sled having: a sled post, at least one contact leg integrally extending from the sled, and opposed first and second sets of legs. The method includes: individually slidably coupling the legs of the first set to the first guide rail, and the legs of the second set to the second guide rail thereby limiting displacement of the sled to only sliding motion in either a loading direction or an opposite ejection direction; positioning the sled having the at least one contact leg in the rail cavity such that the test strip is in direct contact with the contact leg during motion in at least the ejection direction; axially and rotatably connecting the actuator arm to the mechanism assembly; sliding the test strip into the rail cavity; and following completion of a test by the fluid testing device, rotating the actuator arm in an ejection rotational direction thereby displacing the sled in the ejection direction and ejecting the test strip from the fluid testing device.

In a further embodiment of the disclosure, a test strip ejector system for receiving and ejecting a test strip of a fluid testing device includes parallel first and second guide rails defining a rail cavity between the first and second guide rails. A sled has a sled post and opposed first and second sets of legs, each set of legs having multiple S-shaped legs. Each of the S-shaped legs has a convex leg portion in sliding contact with an upper surface, one of the first or second guide rails and an inner concave leg portion in sliding contact with an oppositely facing lower surface of the first or second guide rail to slidably couple the legs to either the first or second guide rail, thereby limiting displacement of the sled to only sliding motion in either a loading direction or an opposite ejection direction. An actuator arm is rotatably connected to a mechanism assembly. The sled post is slidably disposed in an elongated slot of the actuator arm and thereby contacts the actuator arm such that rotation of the actuator arm in a loading rotational direction slides the sled in the loading direction. Subsequent opposite rotation of the actuator arm in an ejection rotational direction displaces the sled in the ejection direction to eject the test strip.

In further embodiments, a glucose test meter has a test strip ejector system for receiving and ejecting a test strip. The test meter includes a meter body having a component board positioned therein. Parallel first and second guide rails are connected to the component board. The first and second guide rails define a rail cavity between the guide rails. A sled has a sled post, first and second contact legs extending into the rail cavity, and opposed first and second legs. Each of the legs is connected externally to and is slidably coupled with respect to one of the first or second guide rails thereby limiting displacement of the sled to only sliding motion in either a loading direction or an opposite ejection direction. A test strip when disposed in the rail cavity directly contacts the contact legs during motion in at least the ejection direction motion. An actuator arm is rotatably connected to a mechanism assembly. The sled post contacts the actuator arm such that rotation of the actuator arm in a loading rotational direction causes sliding motion of the sled in the loading direction and positions the sled in a test strip test position. Opposite rotation of the actuator arm in an ejection rotational direction operates to displace the sled in the ejection direction and to eject the test strip.

In other embodiments, the sled can further include a friction reduction coating applied at least to a surface of the sled having the convex leg portion and the inner concave leg portion of each of the deflectable legs. The sled can also include integrally connected first and second contact legs, the first and second contact legs extending into the rail cavity and in direct contact with the test strip during motion in both the loading and ejection direction motions. The sled can further include a closure member, which when the first and second contact legs contact the closure member defines a positive stop preventing further sliding movement of the sled in the ejection direction. A cover plate positioned in the rail cavity when contacted by the first and second contact legs defines a positive stop preventing further sliding movement of the sled in the loading direction. An elongated slot created in the actuator arm receives the sled post and slidably retains the sled post in the elongated slot. According to several aspects, the sled post is a polymeric material and the sled is a metal, with the sled post being fixedly connected to the sled.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 5 shows a top front left perspective view of a test strip sled of the present disclosure;

FIG. 6 shows a bottom front right perspective view of the test strip sled of FIG. 5;

Figure 1:
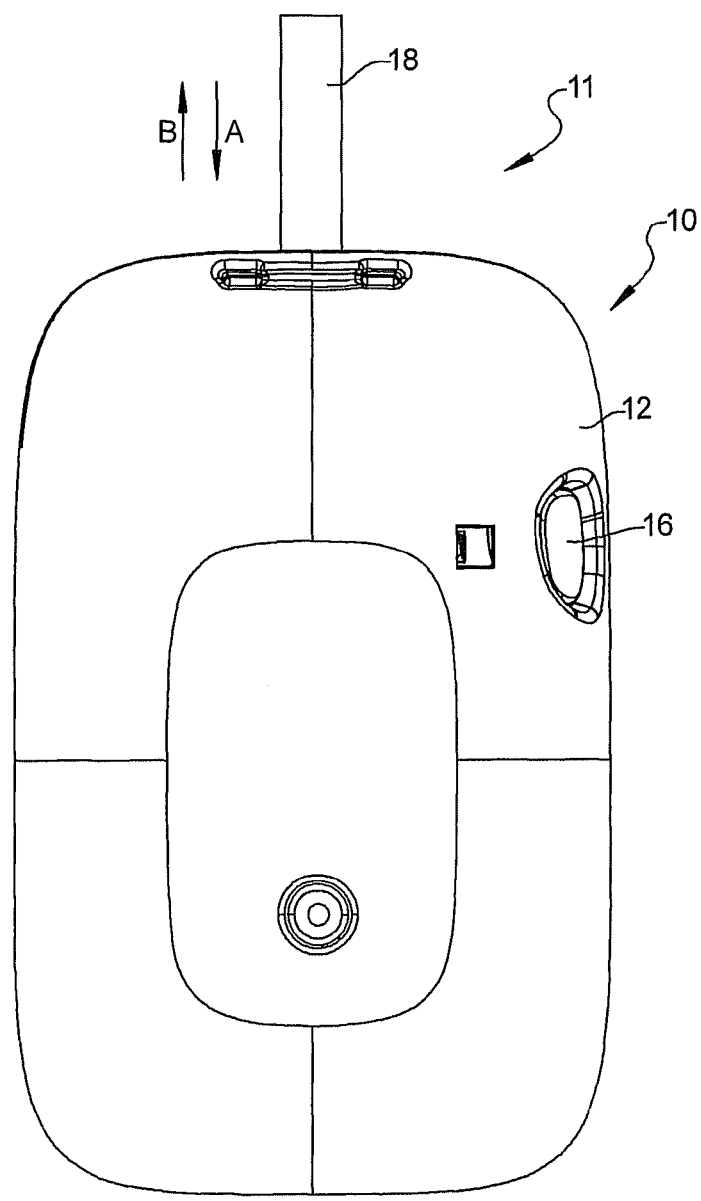
FIG. 1 shows a rear plan view of a fluid analysis device having a test strip ejector of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Referring now to FIG. 1, an analysis device 10 of a test strip ejector system 11, which can be used for example for testing blood glucose levels, includes a housing 12 upon which a digital readout is provided indicating the results of a body fluid test conducted by the analysis device 10. An ejection button 16 is depressed following completion of the test to eject a test strip 18 which was previously received in a loading direction "A" in housing 12. Upon depression of the ejection button 16, the test strip 18 is ejected in an ejection direction "B". The user of the test strip 18 initially inserts test strip 18 into analysis device 10 so the test strip 18 is recognized, and then removes and doses and then again manually inserts the dosed test strip 18 in the loading direction "A". After analyses, subsequent operation of ejection button 16 ejects the test strip 18. Alternately, the user can manually pull the test strip 18 in the ejection direction "B" to manually remove the test strip.

Figure 2:
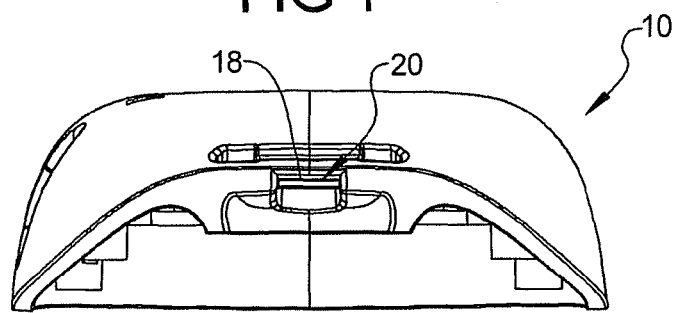
FIG. 2 shows a front elevational end view of the analysis device of FIG. 1.

Referring to FIG. 2, test strip 18 is slidably received via a test strip receiving port 20 created in a first end of analysis device 10. The test strip receiving port 20 is sized to slidably receive the test strip 18 while generally preventing twisting or rotation, such as a racking rotation, due to lateral or side-to-side displacement of the test strip.

Referring to FIG. 3 and again to FIGS. 1 and 2, with the housing 12 removed for clarity, the components of a circuit board assembly 22 are visible. Circuit board assembly 22 includes a printed circuit board 24 such as a printed circuit board having multiple components attached thereto. Housing 12 further includes a mechanism assembly 26 which can be biased prior to or upon receipt of the test strip 18 and can apply a displacement force or a biasing force to eject the test strip 18. Mechanism assembly 26 includes ejection button 16 and an axially rotatable mounting pin 28 which is rotatable with respect to a longitudinal pin center axis 30 which is affixed to a stationary component which would be on the PCB, housing, or some other nearby component. A member such as an actuator arm 32 is connected to mounting pin 28 and therefore co-rotates as mounting pin 28 axially rotates with respect to longitudinal pin center axis 30. The ejection button 16 is biased using an ejection button biasing member 34 to return to the extended position shown following depression by the user. Manual depression of ejection button 16 causes mounting pin 28 and therefore actuator arm 32 to rotate, which directly contacts and slidably displaces a sled 36 in the ejection direction "B". The sled 36 is slidably and connectably engaged with respect to opposed and parallel oriented first and second guide rails 38, 40. First and second guide rails 38, 40 are fixedly connected to printed circuit board 24. The sled 36 slides with respect to and is externally engaged to each of the first and second guide rails 38, 40, as will be better described in reference to FIGS. 11 and 12. A sled post 42 which is generally cylindrical in shape is directly and fixedly connected to sled 36 and is slidably and rotatably received within an elongated slot 44 created in actuator arm 32.

Figure 3:
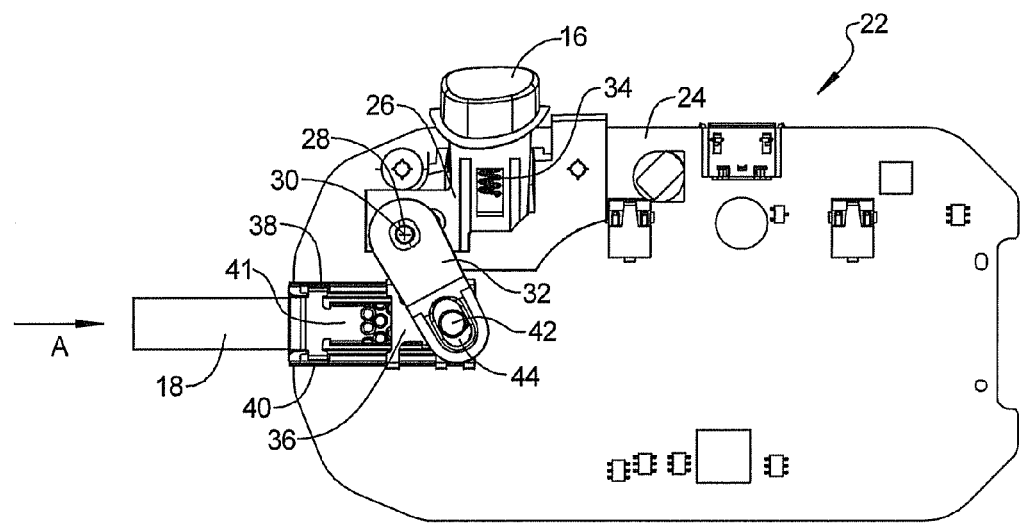
FIG. 3 shows a top plan view of a circuit board assembly and test strip ejector of the analysis device of FIG. 1, with the test strip ejector in the default/test position.

Referring to FIG. 4 and again to FIGS. 1-3, after completion of the test by the analysis device 10, the test strip 18 is ejected from housing 12 by depression of ejection button 16. Actuator arm 32 rotates in a clockwise direction as viewed in FIG. 4 having sled post 42 engaged with sled 36 within elongated slot 44, displacing sled 36 in the ejection direction "B" and thereby discharging test strip 18. The amount of force applied by the user to ejection button 16 determines the force applied by actuator arm 32 and sled post 42 to sled 36 to eject test strip 18. The higher the applied force, the greater the velocity of ejection of test strip 18. Therefore, the force received (Fr) to eject the test strip 18 is a function of the force applied (Fa) to ejection button 16 which is greater than the opposing biasing force (Fo) of ejection button biasing member 34 (Fr=Fa−Fo). Test strip 18 can therefore be ejected with enough force/velocity to direct test strip 18 into a trash or biohazard container (not shown) when not positioned directly over the container, or if analysis device 10 is held directly over the trash or biohazard container, a reduced force applied to ejection button 16 will push test strip 18 out to subsequently fall by gravity. When ejection button 16 is released, the biasing force of ejection button biasing member 34 returns ejection button 16 to its fully extended position.

Figure 13:
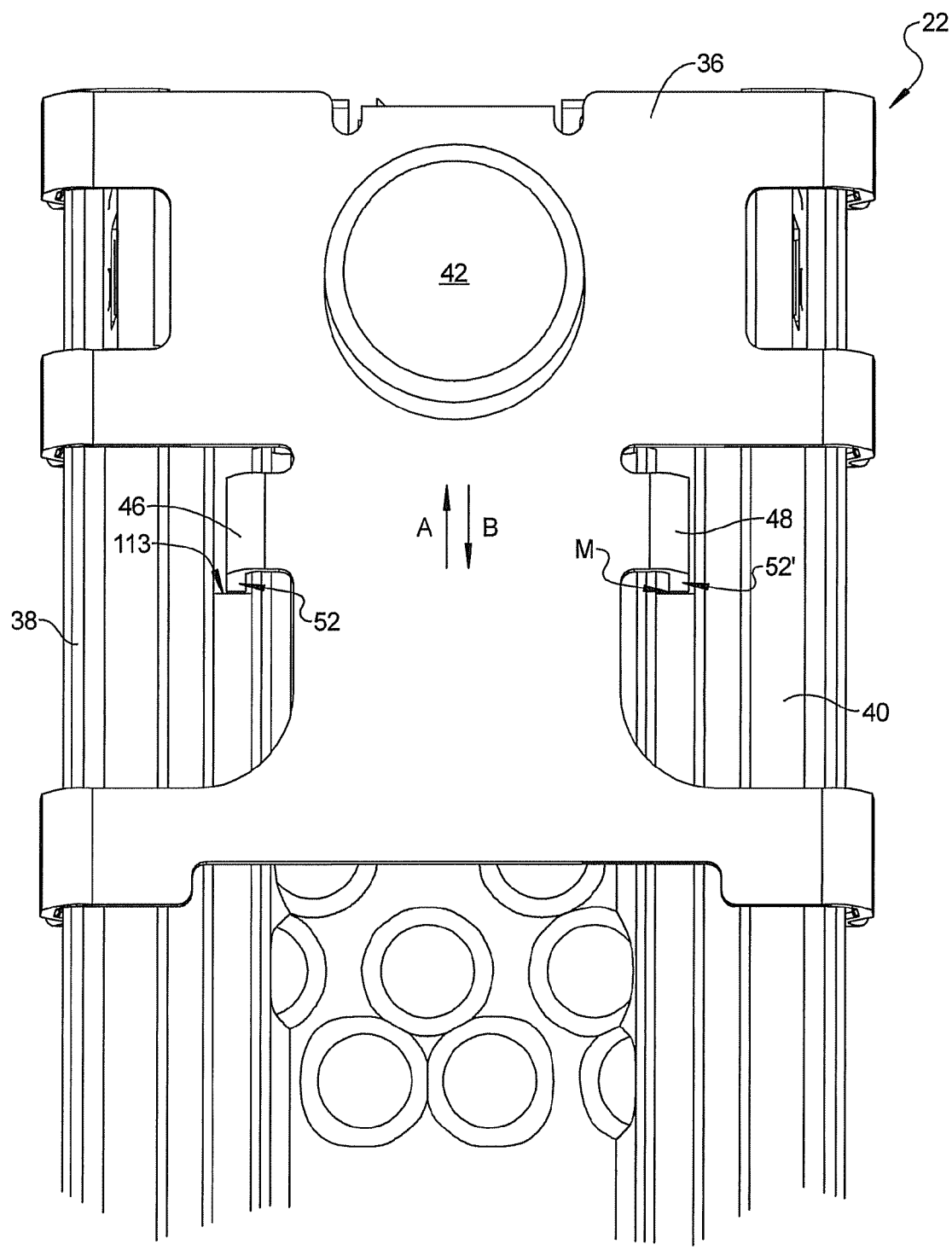
FIG. 13 shows a rear left end perspective view of the test strip eject mechanism of FIG. 12.

With continuing reference to FIG. 3, the actuator arm 32 is shown in a test strip analysis position reached by a counterclockwise rotation with respect to longitudinal pin center axis 30. The test strip analysis position can be provided in each of two aspects. In a first aspect, in addition to biasing ejection button 16, actuator arm 32 is also normally biased by ejection button biasing member 34 to the counterclockwise rotated position shown in FIG. 3, which prepositions the actuator arm 32 and the sled 36 in a neutral position (defined in this aspect as the position shown in FIG. 3) ready for receipt of test strip 18. In this aspect, test strip 18 is freely manually loaded into housing 12 until a strip end contacts or nearly contacts the sled 36. In the neutral position of sled 36 defined in reference to the first aspect test position, it is desirable that a clearance be retained between the test strip 18 and sled 36 during the analyses phase (which is shown and described in reference to FIG. 13). After testing/analyses is complete, ejection button 16 is depressed against the biasing force of ejection button biasing member 34, causing rotation of actuator arm 32, and the sled 36 is displaced in the ejection direction "B" thereby discharging test strip 18.

Figure 4:
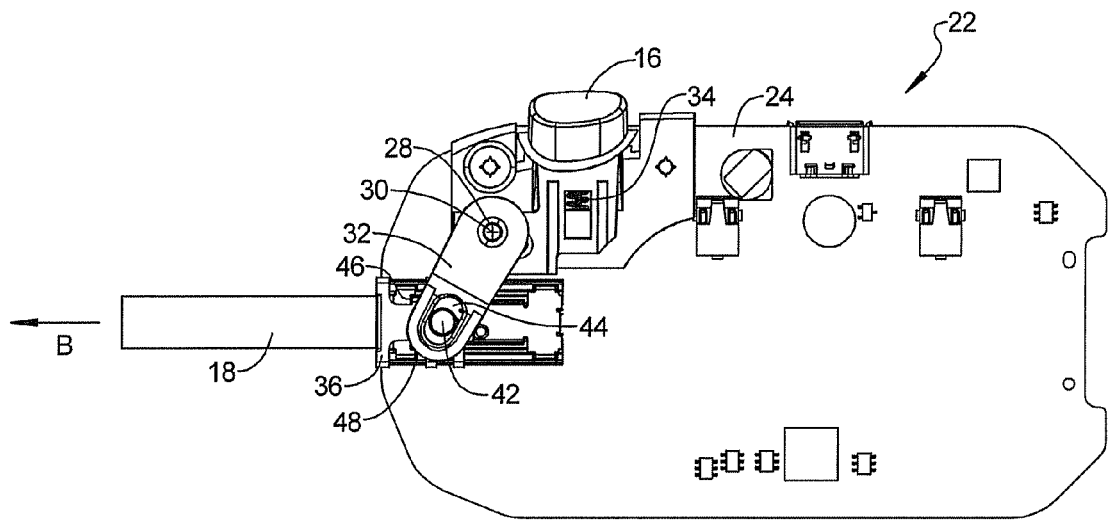
FIG. 4 shows a top plan view of the circuit board assembly and test strip ejector similar to FIG. 3, after the test strip ejector is displaced to the ejection position.

With continuing reference to FIGS. 3 and 4, the test strip analysis position shown in FIG. 3 in a second aspect is reached by displacing sled 36 in the loading direction "A" from an initial position of sled 36 as shown in FIG. 4 by manual insertion of the test strip 18. The force of insertion of test strip 18 slidably displaces sled 36 in the loading direction "A" which directly rotates the actuator arm 32 in a counterclockwise direction. As the test strip 18 is inserted in the loading direction "A", contact between test strip 18 and sled 36 occurs in a rail cavity 41 which is created between the first and second guide rails 38, 40. The elongated slot 44 permits actuator arm 32 to rotate with respect to longitudinal pin center axis 30 in response to a load applied from a sliding motion in the loading direction "A" of both the test strip 18 and sled 36. In this aspect, the sliding motion of sled 36 is therefore translated into a rotational motion of actuator arm 32 by contact between sled post 42 and the wall of elongated slot 44.

Displacement of ejection button 16 causes rotation of the mounting pin 28 in a clockwise direction as viewed with respect to FIG. 4. As the actuator arm 32 rotates in the clockwise direction, a force is applied via contact between actuator arm 32 and sled post 42 such that the rotational motion of actuator arm 32 is translated into an axial sliding motion of test strip 18 in the ejection direction "B". The test strip 18 which is in direct contact with sled 36 is ejected in the ejection direction "B" as the sled 36 is induced to slide in the ejection direction "B". The test strip 18, during test strip loading in the second aspect described above, and during the ejection step for both aspects, is in direct contact with each of opposed first and second contact legs 46, 48 which are substantially rigid, integrally connected to sled 36, and positioned between deflectable legs which will be described in reference to FIG. 5. Test strip 18 when positioned within rail cavity 41 directly contacts first and second contact legs 46, 48 which extend from sled 36 into rail cavity 41.

Referring to FIG. 5, the first and second contact legs 46, 48 are oppositely positioned in a mirror image configuration of each other and have common individual features therefore, the following discussion of first contact leg 46 applies equally to second contact leg 48. First contact leg 46 is substantially rigid and includes a planar leg portion 50 having a contact face 52 facing away from sled post 42. The contact face 52 of each of the first and second contact legs 46, 48 directly contacts the test strip 18 for initially displacing the sled 36 in the loading direction "A" in the second aspect discussed herein, and for ejecting the test strip 18 from analysis device 10 in both the first and second aspects. The provision of the two spaced apart contact faces 52, 52' of the first and second contact legs 46, 48 eliminates induced torque on sled 36 that would occur using only a single contact point of a single pin or leg, therefore further reducing the chance of racking the sled 36 during ejection.

The sled post 42 has a cylindrical body 54 which is perpendicularly oriented with respect to a planar body portion 56 of sled 36. According to several embodiments, sled 36 is made of a metal such as stainless steel, to maximize a stiffness-to-weight ratio of sled 36. Other materials for sled 36 can also be used, including plastics. According to several aspects sled post 42 is created of a polymeric material having a low coefficient of friction such as polyoxymethylene (POM). A POM material or a similar material having a low coefficient of friction is selected for sled post 42 to maintain the shape of sled post 42 and to minimize frictional resistance between sled post 42 and actuator arm 32 as sled post 42 slides within elongated slot 44 and as actuator arm 32 rotates with respect to sled post 42. According to other aspects, in lieu of a separate part, sled post 42 can be an integral extension of the material of sled 36 and made such as by a staking, drawing or similar process during manufacture of sled 36. In these aspects, sled post 42 can be cylindrical, dome shaped, or other shape as the manufacturing process allows. In these aspects, it is also desirable to provide a coating of a material such as polytetrafluoroethylene (PTFE) at least on sled post 42 to minimize frictional resistance between sled post 42 and actuator arm 32.

With continuing reference to FIG. 5 and again to FIGS. 3 and 4, sled 36 includes proximately positioned first and second legs 58, 60 and oppositely proximately positioned third and fourth legs 62, 64 which are in mirror image configuration with respect to first and second legs 58, 60. The sled post 42 according to several aspects is centrally located with respect to each of the first, second, third, and fourth legs 58, 60, 62, 64. A fifth leg 66 can also be provided in a spaced apart relationship with respect to first and second legs 58, 60 such that first leg 58, second leg 60, and fifth leg 66 define a first side leg set 67. Similarly, a sixth leg 68 can be provided in a spaced apart relationship with respect to third and fourth legs 62, 64 such that third leg 62, fourth leg 64, and sixth leg 68 together define a second side leg set 69. Second side leg set 69 is a mirror image of first side leg set 67. According to several aspects, third and fourth legs 62, 64 are omitted, such that only first and second legs 58, 60 and fifth and sixth legs 66, 68 are provided to slidably engage the first and second guide rails 38, 40.

Each of the individual legs 58, 60, 62, 64, 66, 68 have a common geometry, therefore the following discussion of sixth leg 68 applies also to each of the first through fifth legs 58, 60, 62, 64, 66. Each of the legs 58, 60, 62, 64, 66, 68 is positioned oppositely about planar body portion 56 with respect to sled post 42 and is therefore oriented downwardly as viewed in FIG. 5. Each of the legs includes an inner concave leg portion 70 directly connected to an engagement portion 72 which is oppositely directed with respect to inner concave leg portion 70. Directly connected to engagement portion 72 is an end portion 74 which is oppositely directed with respect to engagement portion 72 such that inner concave leg portion 70, engagement portion 72, and end portion 74 together substantially define an S-shaped portion when viewed from an end of sled 36 as will be evident in FIG. 8. It is noted that first and second contact legs 46, 48 which are substantially rigid, are positioned, in the embodiment having six deflectable legs, between the second and fifth legs 60, 66 or the fourth and sixth legs 64, 68, and do not include any of the S-shaped portion features of inner concave leg portion 70, engagement portion 72, or end portion 74.

Referring to FIG. 6 and again to FIG. 5, sled post 42 includes a post connection end 76 which extends through planar body portion 56 such that post connection end 76 is positioned on a lower body face 78 side of planar body portion 56. Post connection end 76 can be mechanically connected to planar body portion 56 using a plurality of connection methods, including staking, forming or adhesively boding, to fix post connection end 76 with respect to planar body portion 56. In addition, a post retainer 80 can also be included with post connection end 76, which can be biased into contact with planar body portion 56 or displaced, such as by a staking operation, such that post retainer 80 acts as a retention member to further retain the fixed position of post connection end 76. According to additional embodiments, a friction reduction coating 81 made from a material having a low coefficient of friction, such as polytetrafluoroethylene (PTFE), can be provided as a coating on at least the lower body face 78 of planar body portion 56. Friction reduction coating 81 can also be provided on both sides or faces of sled 36 prior to or following formation of any of the legs.

Figure 7:
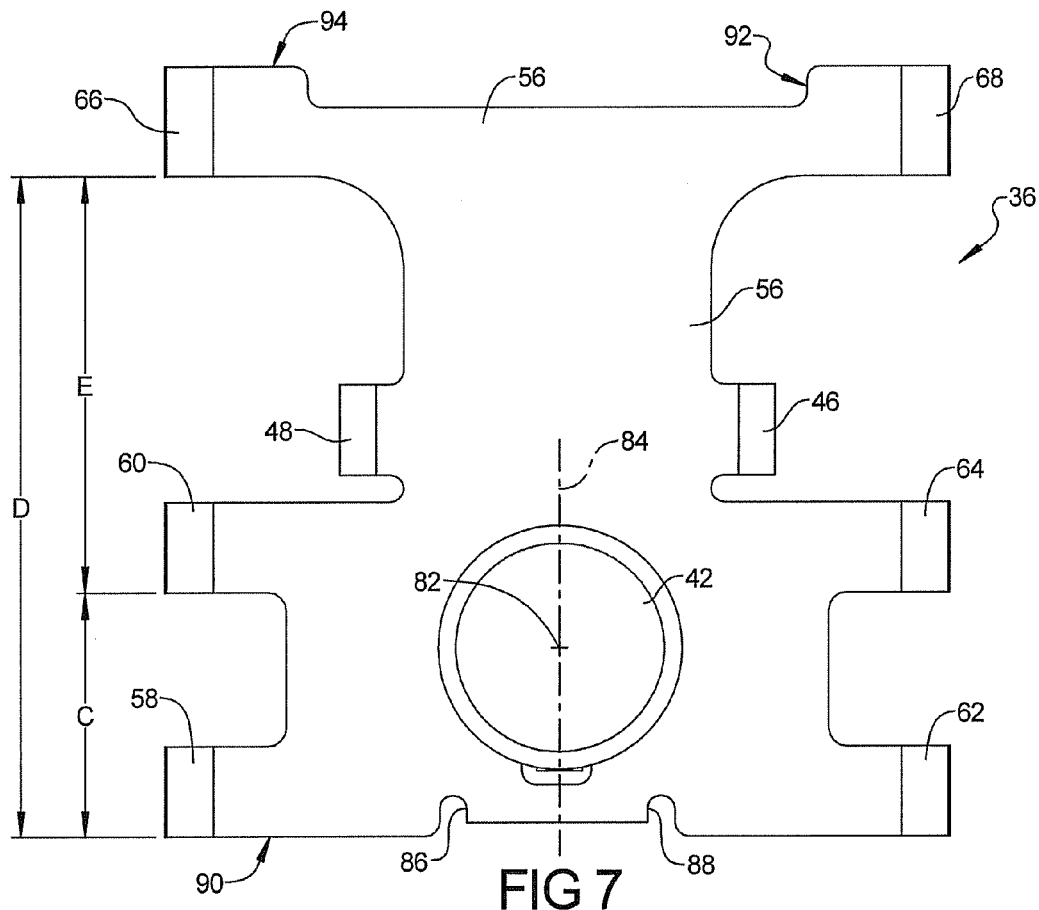
FIG. 7 shows a top plan view of the test strip sled of FIG. 5.

Referring to FIG. 7 and again to FIGS. 5-6, as previously noted sled post 42 is centrally positioned with respect to each of the first and second legs 58, 60 and third and fourth legs 62, 64 such that a longitudinal post central axis 82 of sled post 42 is aligned with a sled longitudinal axis 84. According to additional aspects, features such as first and second body notches 86, 88 can be created at a body first end 90 of planar body portion 56. First and second body notches 86, 88 define a location where material for individual sleds 36 can be perforated from a strip of material (not shown) defining multiple ones of sleds 36. In addition, a third body notch 92 can be created at a body second end 94 of planar body portion 56. The purpose for third body notch 92 will be better described in reference to FIG. 14. According to several embodiments, a first leg-to-leg spacing "C" is provided between first and second legs 58, 60 and also with respect to third and fourth legs 62, 64. A second leg-to-leg spacing "D" is provided between each of first leg 58 and third leg 62 and both fifth leg 66 and sixth leg 68, respectively. Second leg-to-leg spacing "D" is selected such that a third leg-to-leg spacing "E" between, for example, second leg 60 and fifth leg 66 is greater than first leg-to-leg spacing "C". The purpose for this increased spacing used for second leg-to-leg spacing "D" will be described in better detail in reference to FIGS. 12 and 14.

It is noted that the location of first and second contact legs 46, 48, positioned between second and fourth legs 60, 64 and fifth and sixth legs 66, 68, can be positioned at any distance with respect to longitudinal post central axis 82, however, to help mitigate against a racking or rotation motion of sled 36 during operation, the first and second contact legs 46, 48 are positioned as close as possible with respect to longitudinal post central axis 82, while providing clearance for die or stamp tooling during creation of these legs. Racking is defined herein as axial rotation of sled 36 with respect to longitudinal post central axis 82, which if occurring could cause the sled 36 to bind during sliding travel on the first and second guide rails 38, 40, or cause frictional resistance to sliding displacement, particularly during test strip ejection operation when rapid sliding motion is desired. It is noted the description of the legs as first, second, third, fourth, fifth, and sixth legs is for clarity in collectively describing all six of the legs according to one embodiment, however, the legs on any one side of sled 36 such as legs 58, 60, 66 can also be referred to as first, second and third legs in defining their order.

Referring to FIG. 8 and again to FIGS. 3 and 5-7, sled post 42 and its longitudinal post central axis 82 are oriented substantially perpendicular with respect to a body upper surface 96 of planar body portion 56. Each of the first and second contact legs 46, 48 are oriented substantially parallel with respect to longitudinal post central axis 82 and therefore are oriented substantially perpendicular with respect to body upper surface 96 and lower body face 78. Each of the first through sixth legs 58, 60, 62, 64, 66, 68 have similar features with respect to first and third legs 58, 62 shown, therefore the following discussion applies equally to each of the first through sixth legs. A first upper contact surface 98 is defined in inner concave leg portion 70', and an oppositely located second upper contact surface 100 is provided with inner concave leg portion 70'' such that an upper contact surface spacing dimension "G" is defined between first and second upper contact surfaces 98, 100. A first lower contact surface 102 is provided with inner concave leg portion 70', and an oppositely positioned second lower contact surface 104 is provided with inner concave leg portion 70''. A lower contact surface spacing dimension "H" is greater than the upper contact surface spacing dimension "G", thereby defining an outwardly canted angle α for inner concave leg portion 70'' which is duplicated but oppositely directed with respect to inner concave leg portion 70'. The difference between upper and lower contact surface spacing dimensions "G", "H" helps prevent binding of the individual legs during sliding motion of sled 36. A spacing or distance dimension between engagement portions 72', 72'' is less than each of the upper or lower contact surface spacing dimensions "G", "H". The S-shape of each of the legs 58, 60, 62, 64, 66, 68 including engagement portion 72 externally contacts and captures one of the guide rails 38, 40, which together with the deflectable design of the legs thereby provides continuous, positive contact between the legs with the guide rails 38, 40 throughout the travel path of sled 36, and limiting displacement of the sled 36 to only sliding motion in either the loading direction "A" or the opposite ejection direction "B", and further preventing the sled 36 from moving away from the guide rails 38, 40 during sliding motion.

Referring to FIG. 9 and again to FIG. 3, sled 36 is shown in the test strip 18 loaded or test/analysis position such that a plane 106 extending through planar body portion 56 of sled 36 is oriented parallel to each of test strip 18 and printed circuit board 24. Actuator arm 32 rotates parallel with respect to plane 106, which therefore minimizes the potential for binding or racking of sled 36 as it receives or ejects test strip 18.

Figure 9:
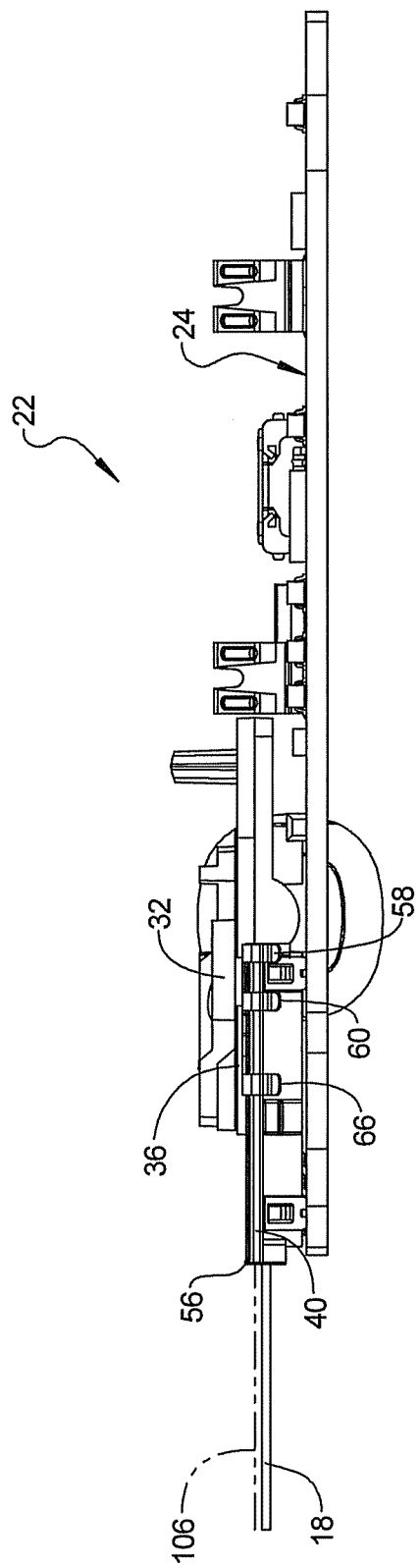
FIG. 9 shows a side elevation view of the circuit board assembly of FIG. 3.

Referring to FIG. 10 and again to FIGS. 3 and 9, as test strip 18 is slidably moved within rail cavity 41, sled 36 is free to slidably displace either toward or away from the viewer, as shown in reference to FIG. 10. Sled 36 is slidable but is contained with respect to a "Z" axis by sliding engagement of inner concave leg portion 70' with respect to an outward facing first guide rail bulbous face 108 of first guide rail 38, and with respect to inner concave leg portion 70'' by sliding engagement with respect to an outward facing second guide rail bulbous face 110 of second guide rail 40. First and second guide rail bulbous faces 108, 110 are oppositely directed with respect to each other, and each of the first and second guide rails 38, 40 are oriented substantially perpendicular with respect to a board planar surface 112 of printed circuit board 24.

Figure 10:
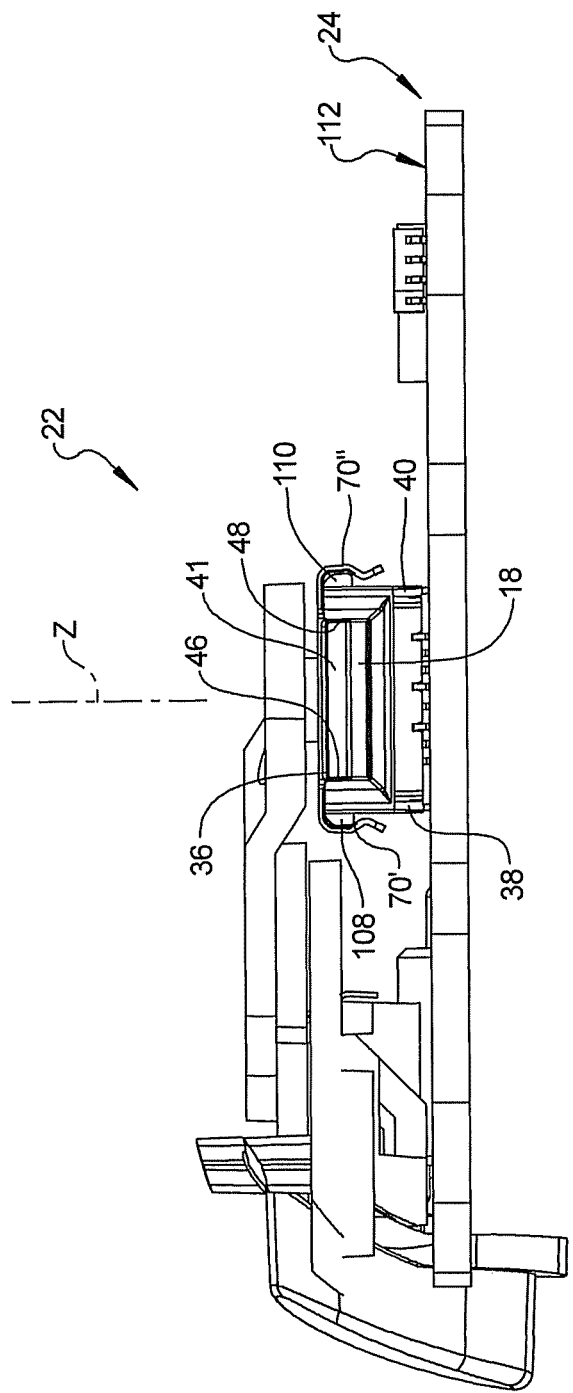
FIG. 10 shows a front end elevation view of the circuit board assembly of FIG. 3.

Referring to FIG. 11 and again to FIGS. 3 and 10, according to the second aspect described herein, as test strip 18 is slidably disposed into the test strip receiving port 20 in the loading direction "A", a test strip end wall 113 of test strip 18 directly contacts each of the contact faces 52, 52' of first and second contact legs 46, 48. This direct contact thereafter slidably displaces sled 36 also in the loading direction "A". As sled post 42 of sled 36 is displaced in the loading direction "A", sled post 42 contacts actuator arm 32 in elongated slot 44 and thereby rotates actuator arm 32 in a loading rotational direction "J" with respect to the longitudinal pin center axis 30. For both the first and second aspects, as test strip 18 is received at the test position shown, multiple contact points of the test strip 18 contact a connector 111 positioned in the device thereby making electrical contact with the connector 111 to permit analyses of the fluid provided with test strip 18. Connector 111 can include multiple, individual contact points that each align with one of the contact points of the test strip 18.

Figure 12:
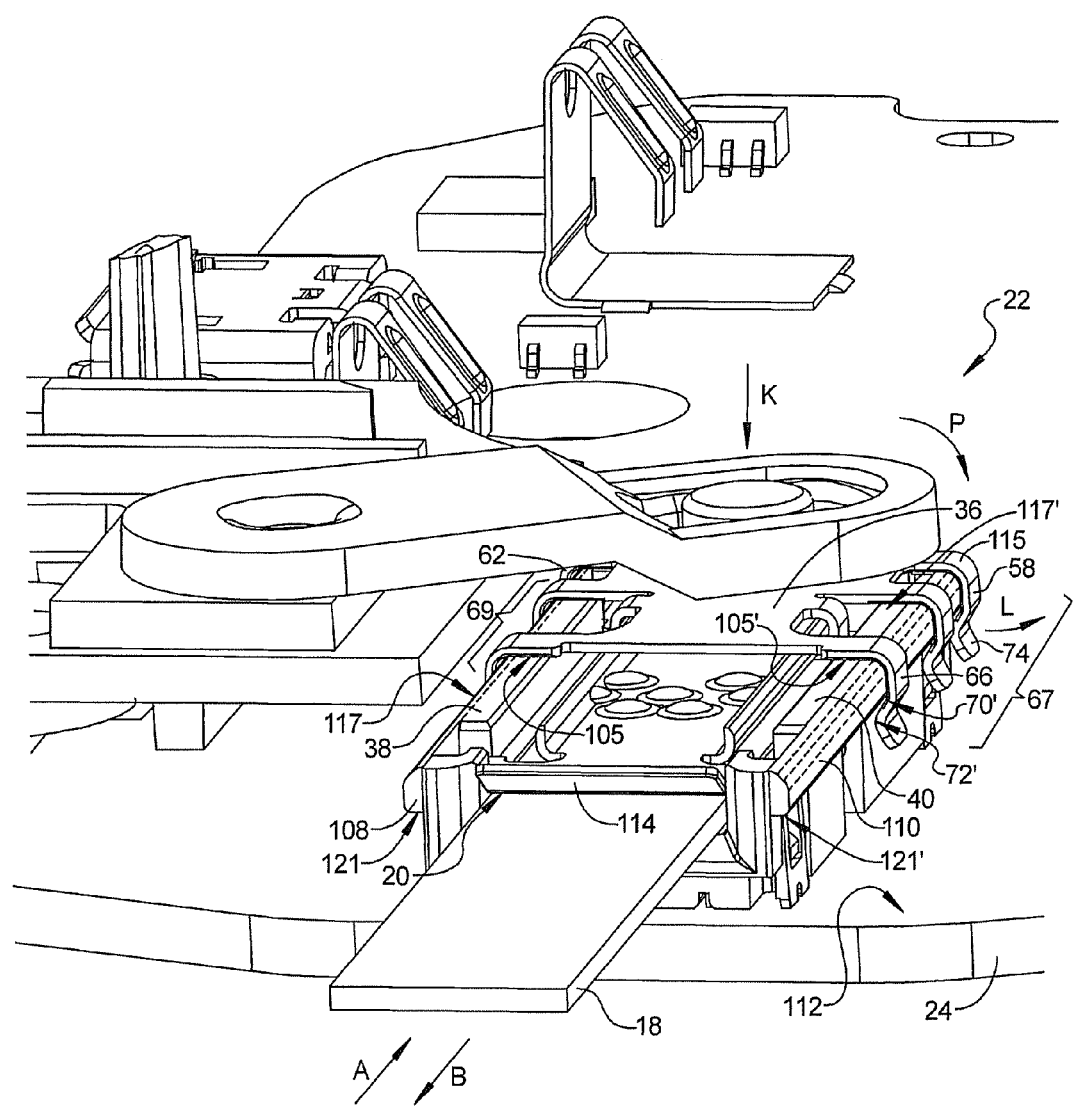
FIG. 12 shows a front right end perspective view of the test strip eject mechanism of FIG. 3.

Referring to FIG. 12, a closure member 114 is provided between first and second guide rails 38, 40 and delineates test strip receiving port 20, and further maintains parallel alignment between test strip 18 and board planar surface 112. Each of the first through sixth legs 58, 60, 62, 64, 66, 68 of sled 36 is positioned having the planar leg faces 105, 105' in sliding contact with upper surfaces 117, 117' of the first and second guide rails 38, 40, and each includes a convex leg portion 115 wrapping partially about the first and second guide rail bulbous faces 108, 110, thereby individually externally connecting each of the first through sixth legs 58, 60, 62, 64, 66, 68 to one the first or second guide rails 38, 40. The inner concave leg portion 70 of each of the first through sixth legs is in sliding contact with an oppositely facing lower surface 121, 121' of either the first or second guide rail bulbous face 108, 110 such that the first through sixth legs 58, 60, 62, 64, 66, 68 partially capture one of the first or second guide rails 38, 40. This partial capture prevents sled 36 from lifting off in a direction perpendicular to the first and second guide rails 38, 40, and prevents the planar leg faces 105, 105' from moving away from sliding contact with the upper surfaces 117, 117' of the first or second guide rails 38, 40 at any position of the sled 36. The engagement portions 72 of each of the first through sixth legs 58, 60, 62, 64, 66, 68 are also positioned in sliding contact with one of the lower surfaces 121, 121' of the first or second guide rail bulbous faces 108, 110 to further mitigate lifting of the sled 36 at any of its sliding positions.

It is noted that the multiple independent legs herein described as first through sixth legs 58, 60, 62, 64, 66, 68 are included in one embodiment of sled 36 however, according to further embodiments, any or all of the individual legs of either first or second side leg sets 67, 69 can be combined together and still include the features of inner concave leg portion 70 and engagement portion 72. Therefore, a single leg, two legs, three legs or more than three deflectable legs can be provided on each side of sled 36. The width and/or dimensions of the single leg or multiple legs on each side can also be varied. For example only, a single leg having a width corresponding to the outside end to outside end spacing of first and fifth legs 58 and 66 can be used in place of first leg 58, second leg 60 and fifth leg 66. The use of multiple individual legs in place of single wide legs reduces surface leg area sliding friction of sled 36 while providing maximum spacing between the end legs, such as first leg 58 and fifth leg 66, which maximizes a moment arm of sled 36, thereby minimizing a racking or rotation of sled 36 as it slides with respect to the first or second guide rails 38, 40. A further advantage of providing the multiple individual legs of the first and second side leg sets 67, 69 is that multiple individual legs provide greater elastic flexibility than single or combined legs. This elastic flexibility allows sled 36 to be mounted during an installation stage in a sled installation direction "K" oriented perpendicular to the first and second guide rails 38, 40, rather than requiring sliding installation in either of the loading direction "A" or ejection direction "B". The legs 58, 60, 62, 64, 66, 68 outwardly elastically deflect about the first and second guide rails 38, 40 allowing installation of the sled 36 in sled installation direction "K" transverse to the loading direction "A" and the ejection direction "B".

Installation via sled installation direction "K" allows sled 36 to be positioned directly over first and second guide rails 38, 40 and installed prior to installation of actuator arm 32 without interfering with any other component mounted on printed circuit board 24, or requiring the other component or components to be temporarily removed and/or installed at a later time than the installation of sled 36. This allows for automated machine installation of sled 36. During installation of sled 36 in the sled installation direction "K", the end portion 74 of each of the individual legs deflects elastically outward with respect to the first or second guide rail bulbous face 108, 110. This allows each leg to elastically deflect in a leg displacement direction "L", as shown for first side leg set 67, and oppositely deflect (not visible in this view) with respect to second side leg set 69. When the engagement portion 72, 72' moves past the first or second guide rail bulbous face 108, 110, the leg elastically snaps back to the non-deflected position. With the engagement portion 72, 72' oppositely positioned about the first or second guide rail bulbous face 108, 110 with respect to the planar leg faces 105, 105', the sled 36 is thereby slidably coupled to the first and second guide rails 38, 40, limiting motion of sled 36 to sliding motion in either of the loading or ejection directions "A", "B".

Referring to FIG. 13 and again to FIG. 12, in the neutral position of sled 36 defined in reference to both the first and second aspects discussed above, test strip 18 is positioned in the fully inserted or test position. A clearance "M" can be provided between the test strip end wall 113 of test strip 18 and the contact faces 52, 52' of first and second contact legs 46, 48 of sled 36 during the test/analyses phase. Provision of clearance "M" prevents any force being applied to test strip 18 in the ejection direction "B" during the test/analysis phase.

Referring to FIG. 14 and again to FIGS. 3-12, third body notch 92 provides clearance for angled entrance lip 116 when sled 36 reaches its furthest displaced ejection position. Although contact between third body notch 92 and angled entrance lip 116 can provide a positive stop for sled 36, according to several aspects, a preferred positive stop for sled 36 is provided by direct contact between first and second contact legs 46, 48 and each of a first and second stop face 118, 119 provided with closure member 114. Following depression of ejection button 16, actuator arm 32 rotates in an ejection rotational direction "N", thereby creating direct contact between a slot wall 120 of elongated slot 44 and an outer or perimeter surface of sled post 42. This contact and counterclockwise rotation of actuator arm 32 displaces sled 36 in the ejection direction "B", allowing ejection or removal of test strip 18. It is noted that sled 36 is prevented from extending past either end of the first or second guide rails 38, 40 by the positive stops created using first and second stop faces 118, 119 and oppositely by contact between first and second contact legs 46, 48 and each of a first and second abutment face 126, 127 provided with a cover plate 128 seated between first and second guide rails 38, 40. Sled 36 therefore cannot extend past rail assembly first end 122 or an opposite rail assembly second end 124 due to the positive stop features. According to other aspects, it is possible to eliminate the positive stop features and prevent displacement of sled 36 past either rail assembly first or second ends 122, 124 by limiting a rotation of mounting pin 28, and thereby limiting rotation of actuator arm 32 between the fully ejected position and the fully loaded position of sled 36.

Figure 8:
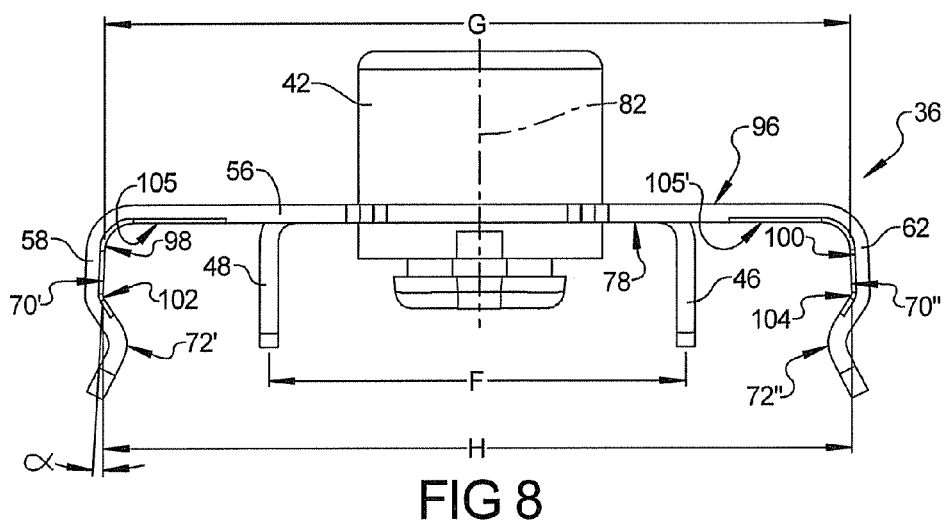
FIG. 8 shows an end elevation view of the test strip sled of FIG. 5.
Figure 14:
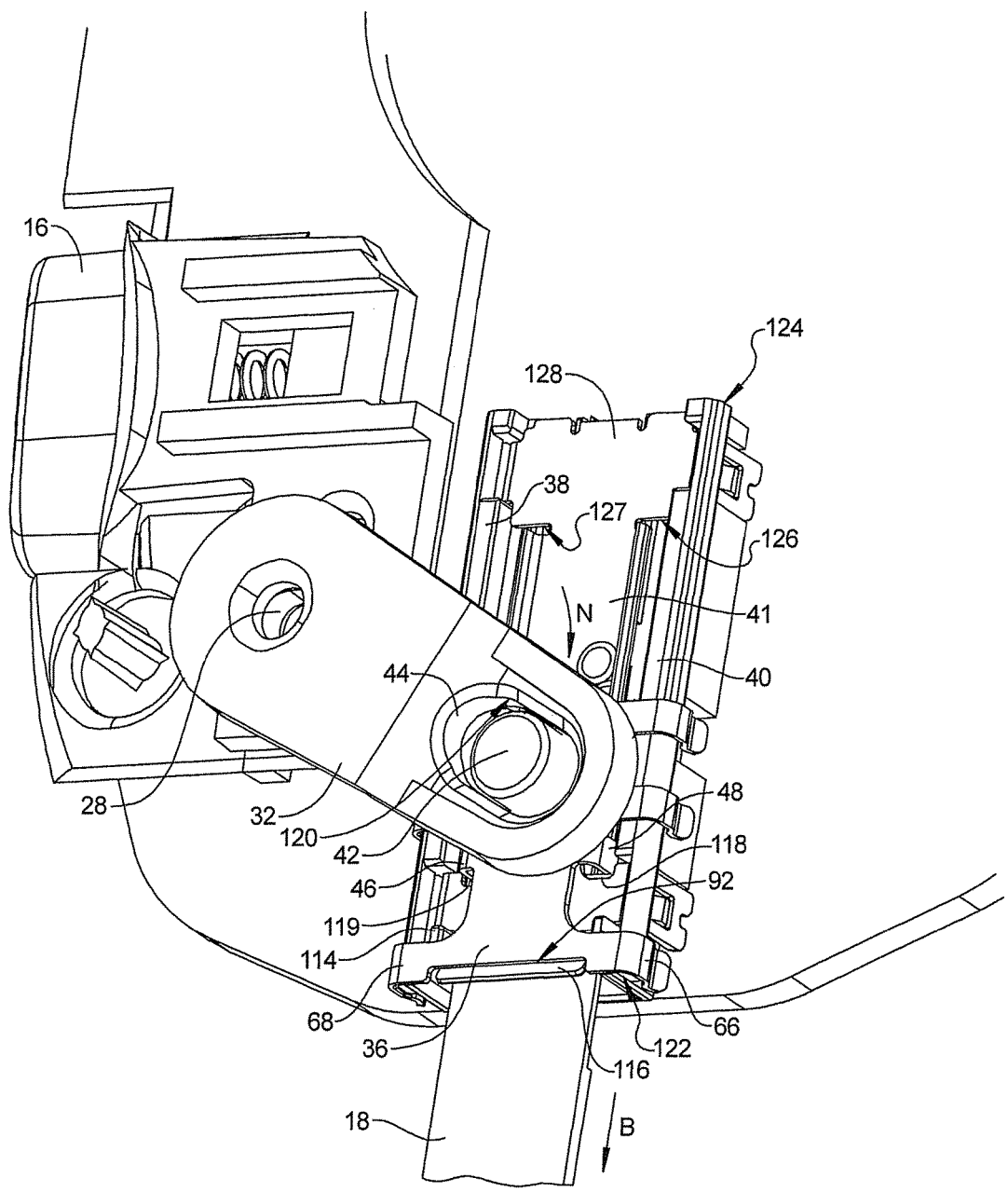
FIG. 14 shows a front right end perspective view of the test strip eject mechanism of FIG. 4.

With continuing reference to FIGS. 8 and 14, the contact leg spacing dimension "F" of first and second contact legs 46, 48 is selected to position first and second contact legs 46, 48 within rail cavity 41 while providing as wide as possible contact leg spacing dimension "F" at the maximum width of test strip 18. This also helps mitigate rotation or racking of sled 36 and/or test strip 18.

For operation, the test strip ejector system 11 for receiving and ejecting test strip 18 from fluid analysis device 10 includes first and second guide rails 38, 40 defining rail cavity 41 between the guide rails 38, 40. Sled 36 includes first and second spatially separated contact faces 52, 52' positioned in the rail cavity 41 and opposed first and second legs 58, 62, each of the legs 58, 62 connected externally to and slidably coupled with respect to one of the first or second guide rails 38, 40 for sled motion in each of the loading direction "A" and the ejection direction "B". Actuator arm 32 is rotatably connected to the fluid analysis device 10. The sled 36 is coupled to the actuator arm 32 such that rotation of the actuator arm 32 in the loading rotational direction "J" moves the sled in the loading direction "A" to position the sled 36 in the test strip test position (shown in FIG. 3). Opposite rotation of the actuator arm 32 in the ejection rotational direction "P" operates to displace the sled 36 in the ejection direction "B" away from the test strip test position and to position the first and second contact faces 52, 52' in direct contact with the test strip 18 to eject the test strip 18 from the fluid analysis device 10.

Figure 11:
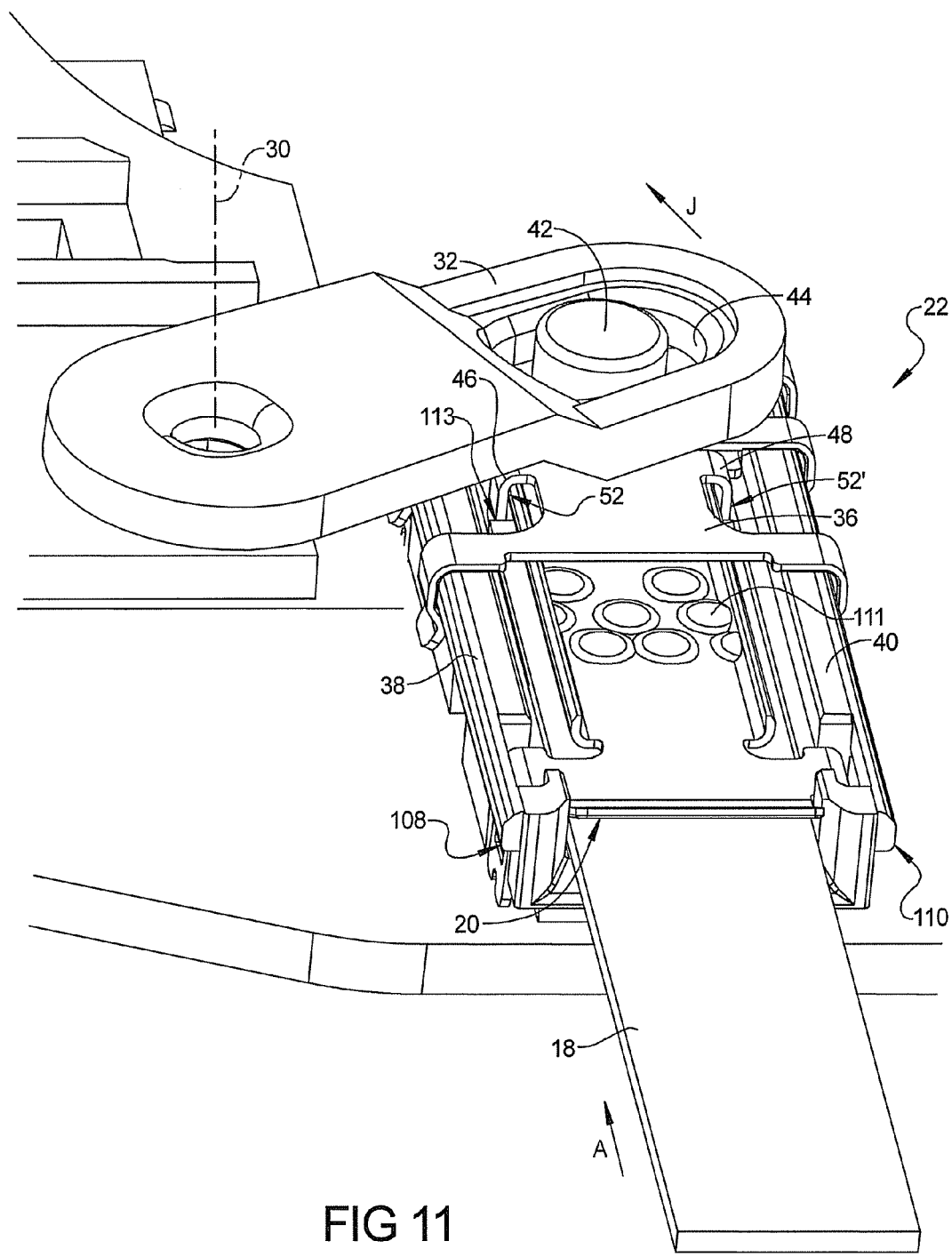
FIG. 11 shows a front left end perspective view of the test strip eject mechanism of FIG. 3.

With continuing reference to FIGS. 5 and 11-14, with the exception of the first and second contact legs 46, 48 of sled 36, the one or multiple individual legs of the first and second side leg sets 67, 69 are each in continuous sliding contact only with one of the first or second guide rails 38, 40 in all reciprocal positions of sled 36, including the test strip test position shown in FIG. 11 and the ejection position shown in FIG. 14, as well as all positions in between. Contact "only with" one of the first or second guide rails 38, 40 as recited above is defined herein to mean that no portion of any of the legs of the first and second side leg sets 67, 69 is in contact with, retained by, or guided by any other feature or structure of the analysis device 10 except the first and second guide rails 38, 40 in any position of sled 36. This further helps to mitigate against racking or binding of sled 36. In addition, no portion of any of the legs of the first and second side leg sets 67, 69 extends longitudinally beyond the first or second ends 122, 124 of first or second guide rails 38, 40 in any operating position of sled 36, therefore the legs are always continuously and completely retained in sliding contact with the first or second guide rails 38, 40. Further clearance for longitudinal motion of sled 36 is therefore not required beyond the extents or first and second ends 122, 124 of first and second guide rails 38, 40. The sled 36 therefore has the first and second spatially separated contact faces 52, 52' located between opposed first and second legs, such as legs 58, 62 of the first and second leg sets 67, 69, wherein each of the legs 58, 62 is connected externally to and retained in sliding continuous contact with one of the first or second guide rails 38, 40 between the first and second ends 122, 124 of the guide rails for sled motion in each of the loading direction "A" and the ejection direction "B".

Referring to FIG. 15 and again to FIGS. 1-14, an analysis device 130 is modified from analysis device 10 to include a sled 132 having four legs in lieu of six legs, including first, second, third and fourth legs 134, 136, 138, 140 which are substantially equivalent to first, third, fifth and sixth legs 58, 62, 66 and 68 of sled 36. The first and second guide rails 38, 40 are removed for clarity. The sled post 42 of sled 132 is rotatably connected to actuator arm 32. First and second contact legs 142, 144 are similarly provided and oriented on sled 132 and therefore perform the same functions as first and second contact legs 46, 48. A raised member 146 extending from housing 12 includes an arc-shaped surface 148 which is directly contacted by sled post 42 and acts as a guide for sled post 42 during displacement of sled 132. The mounting pin 28 is slidably received in a first elongated slot 150 created in an ejection button body extension 152 which is connected to ejection button 16. In the sled neutral position shown, ejection button 16 and ejection button biasing member 34 are fully extended, mounting pin 28 is positioned proximate to a first end of first elongated slot 150, and sled 132 is positioned to receive a test strip 18. A driver pivot pin 154 extends from actuator arm 32, and according to several embodiments is integrally connected to actuator arm 32. Driver pin 154 is received in a second elongated slot 156 created in body extension 152, having a shorter length than first elongated slot 150 to allow limited displacement of driver pin 154 during rotation of actuator arm 32. A stop member 158 connected to structure of housing 12 provides a non-displaceable receiving point for ejection button biasing member 34.

Figure 15:
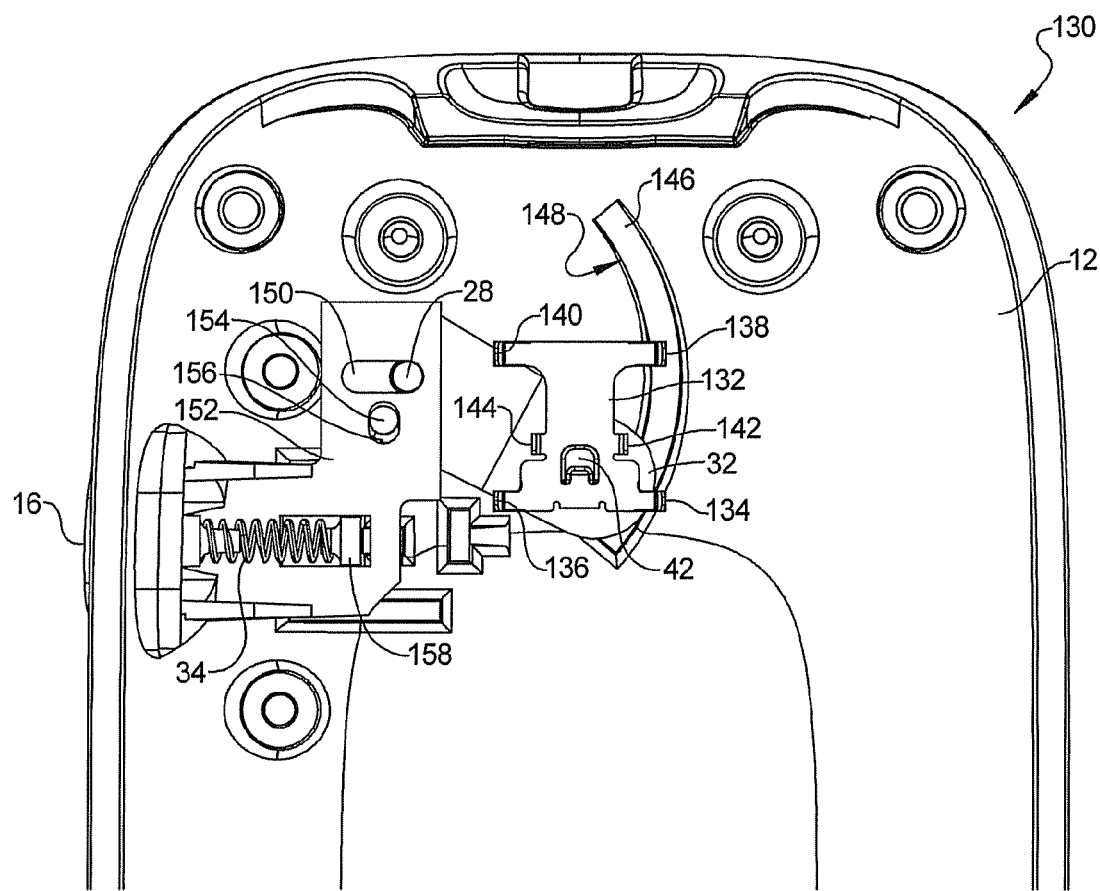
FIG. 15 shows a bottom plan view of a circuit board assembly and test strip ejector modified from the analysis device of FIG. 1, with the test strip ejector in the default/test or neutral position.
Figure 16:
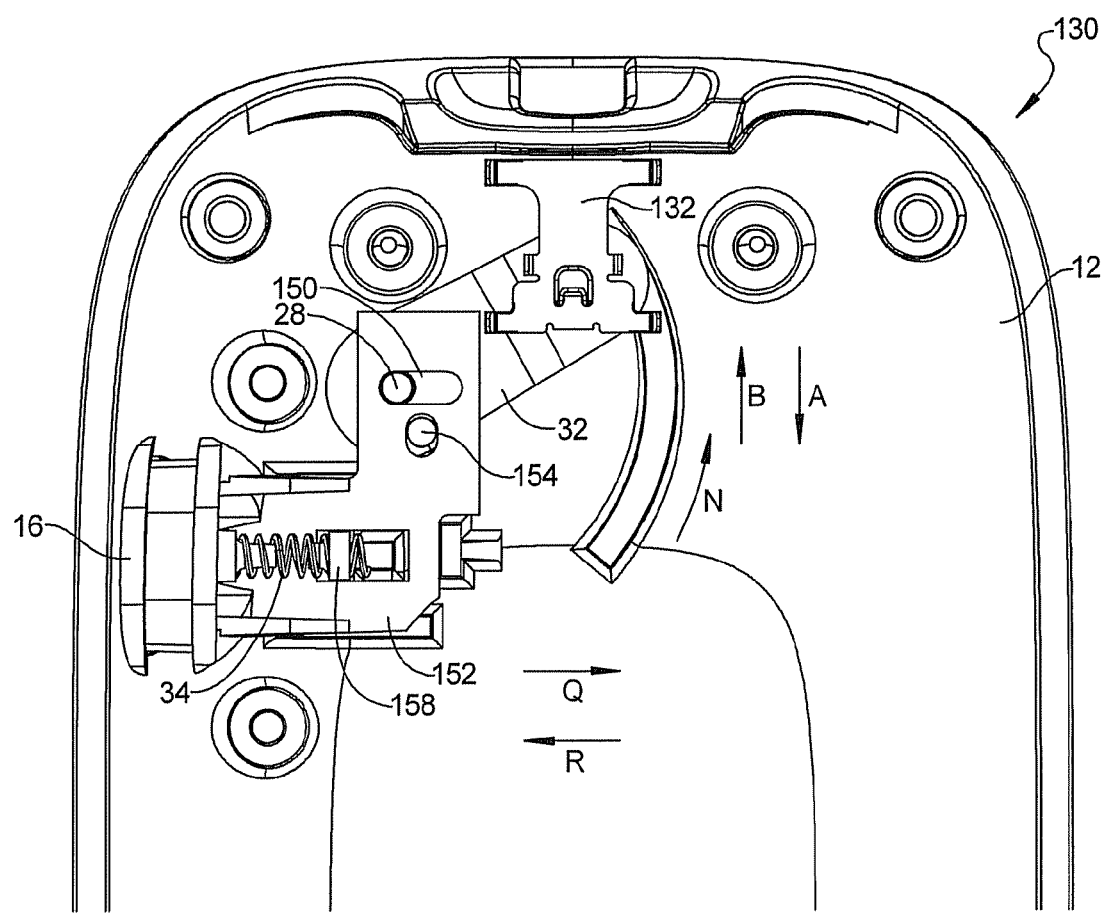
FIG. 16 shows a bottom plan view of the circuit board assembly and test strip ejector similar to FIG. 15, after the test strip ejector is displaced to the ejection position.

Referring to FIG. 16 and again to FIG. 15, ejection button 16 is shown after depression which compresses ejection button biasing member 34 against stop member 158 and slidably displaces ejection button 16 and body extension 152 in a release direction "Q". This motion of body extension 152 also displaces driver pin 154 in the release direction "Q". Because mounting pin 28 is substantially fixed with respect to housing 12, displacement of driver pin 154 in the release direction "Q" rotates actuator arm 32 in the ejection rotational direction "N". Displacement in the release direction "Q" continues until, by the displacement of body extension 152, a second end of first elongated slot 150 is positioned proximate to mounting pin 28 and the positions of mounting pin 28 and driver pin 154 are reversed with respect to their positions in the neutral position shown in FIG. 15. Rotation of actuator arm 32 in the ejection rotational direction "N" displaces sled 132 in the ejection direction "B". Subsequent release of ejection button 16 by the user allows the biasing force of ejection button biasing member 34 to displace body extension 152 and ejection button 16 in a return direction "R", opposite to release direction "Q", thereby returning sled 132 in the loading direction "A" to the neutral position shown in FIG. 15.

As noted herein, test strip ejectors and systems of the present disclosure can be used in meters by individual users having personal test meters. Test strip ejector systems of the present disclosure can also be incorporated in commercial devices such as hospital meters, for example rechargeable test meters recharged by installation in a base unit, and/or blood glucose meters such as ACCU-CHEK® Inform System glucose meters manufactured by Roche Diagnostics. The test strips used by such hospital and glucose test meters can be configured differently from the test strips identified herein to conform to the requirements of the test and/or test meter, however the test strip ejector systems of the present disclosure will be similarly configured and function in a similar manner.

In addition, test strip ejectors and systems of the present disclosure can also be incorporated in individual or commercial devices such as blood coagulant test meters, for example blood clotting time test meters such as the Coagu-Chek® XS System coagulant test meters manufactured by Roche Diagnostics. The test strips used by such blood coagulant test meters can be configured differently from the test strips identified herein to conform to the requirements of the test and/or test meter, however the test strip ejector systems of the present disclosure will be similarly configured and function in a similar manner.

Test strip ejectors of the present disclosure offer several advantages. The following discussion of analysis device 10 applies equally to analysis device 130. Sled 36 of the present disclosure provides a sliding motion member that is retained by its deflectable legs externally to a parallel set of guide rails 38, 40. This provides a clear space or rail cavity 41 between the guide rails for sliding motion of the test strip 18 in direct contact with sled 36. The first and second contact legs 46, 48 of sled 36 extend into rail cavity 41 so continuous contact with test strip 18 is maintained when test strip 18 is positioned in rail cavity 41 during sliding motion, at least in the ejection direction "B". In the neutral position of sled 36 defined in reference to the first aspect test position, a clearance "M" can be maintained between the test strip 18 and sled 36 during the analyses phase to prevent any force being applied to test strip 18 in the ejection direction "B" during the test/analysis phase. According to other aspects, continuous contact between first and second contact legs 46, 48 of sled 36 with test strip 18 can be maintained during all times when test strip 18 is positioned in rail cavity 41. The use of multiple elastically flexible legs 58, 60, 62, 64, 66, 68 extends a moment arm of sled 36 to minimize racking motion while also allowing for installation of sled 36 in a "Z" axis, perpendicular to the orientation of the guide rails. The sled post 42 being received in an elongated slot of actuator arm 32 converts a rotational motion of actuator arm 32 into the sliding motion of sled 36, minimizing the space required for the ejection mechanism assembly 26 on printed circuit board 24, while allowing the ejection mechanism assembly 26 to be mounted to a side of the guide rails in lieu of in axial relationship with the guide rails.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A test strip ejector system for receiving and ejecting a test strip of an analysis device, the system comprising:
    a plurality of guide rails attached to a component board, the plurality of guide rails including at least a first guide rail and a second guide rail, the first and second guide rails being the outermost guide rails of the plurality of guide rails, each of the first and second guide rails including an upper surface, an internal face, and an external face opposite the internal face, the internal faces of the first and second guide rails facing one another to define a rail cavity that is disposed between the first and second guide rails, and the external faces of the first and second guide rails facing away from the rail cavity in opposite directions;
    a sled having opposed first and second body ends and having multiple opposed legs configured to partially capture there between the first and second guide rails, each of the legs positioned externally to and retained in sliding continuous contact with one of the first or second guide rails limiting sled motion to each of a loading direction and an ejection direction;
    a member movably connected to the analysis device, the sled coupled to the member such that member movement in a first direction displaces the sled in the loading direction to position the sled in a test strip test position, and opposite member movement in a second direction operates to displace the sled in the ejection direction away from the test strip test position to eject the test strip from the analysis device by sled travel toward a test strip ejection position; and
    each of the legs having a planar leg face disposed in sliding contact with the upper surface of one of the guide rails and an inner shape selected to contact and at least partially capture the external face of one of the guide rails, thereby limiting displacement of the sled to only sliding motion in either the loading direction or the ejection direction;
    wherein the first and second guide rails are not bounded by any other guide rails in a direction that is transverse to the loading direction and the ejection direction;
    wherein the multiple opposed legs includes at least first and second legs on a first side of a sled longitudinal axis and at least third and fourth legs on a second side of the sled longitudinal axis;
    wherein the sled includes opposed first and second contact legs which are substantially rigid and integrally connected to the sled, the first and second contact legs positioned between the first and second legs and the third and fourth legs;
    wherein the first and second contact legs are positioned within the rail cavity defined between the first and second guide rails, the test strip when positioned within rail cavity directly contacting the first and second contact legs.

2. The system of claim 1, wherein the legs include at least one bend defining an engagement portion and include a convex leg portion in sliding contact with an upper surface of one of the first or second guide rails.

3. The system of claim 2, wherein the at least one bend of each of the legs further includes an inner concave leg portion in sliding contact with an oppositely facing lower surface of the first or second guide rail.

4. The system of claim 1, wherein each of the legs includes an engagement portion externally contacting and partially capturing the face of one of the guide rails between first and second ends of the guide rails.

5. A glucose test meter having a test strip ejector system for receiving and ejecting a test strip, the test meter comprising:
    a meter body having a component board positioned therein;
    a plurality of guide rails including a first guide rail and a second guide rail, the first and second guide rails being the outermost guide rails in the plurality of guide rails, the first and second guide rails being parallel to one another, the first and second guide rails being connected to the component board, and the first and second guide rails defining a rail cavity between the guide rails;
    a sled having a sled post, first and second contact legs extending into the rail cavity, and opposed first and second leg sets positioned externally to and slidably coupled with the first or second guide rails thereby limiting displacement of the sled to only sliding motion in either a loading direction or an opposite ejection direction, each of the legs having a shape selected to externally contact and partially capture a face of one of the guide rails, a test strip when disposed in the rail cavity directly contacting the contact legs during motion in at least the ejection direction motion; and
    an actuator arm rotatably connected to the meter body, the sled post contacting the actuator arm such that sliding motion of the sled in the loading direction and rotation of the actuator arm in a loading rotational direction positions the sled in a test strip test position, and opposite rotation of the actuator arm in an ejection rotational direction operates to displace the sled in the ejection direction and to eject the test strip;
    wherein the first and second guide rails are not bounded by any other guide rails in a direction that is transverse to the loading direction and the opposite ejection direction of the sled;
    wherein the sled includes a post received in an elongated slot of the actuator arm to retain the sled in contact with the actuator arm during motion in both the loading and ejection directions.

6. The glucose test meter of claim 5, further including an ejection button connected to the mechanism assembly depressed to rotate the actuator arm in the ejection rotational direction.

7. The glucose test meter of claim 5, wherein the component board is a printed circuit board.

8. The glucose test meter of claim 5, wherein each of the first and second guide rails has an external face, the external faces of the first and second guide rails facing away from one another and away from the rail cavity that is defined between the first and second guide rails.

9. A test strip ejector system for receiving and ejecting a test strip of an analysis device, the system comprising:
    a plurality of guide rails attached to a component board, the plurality of guide rails including at least a first guide rail and a second guide rail, the first and second guide rails being the outermost guide rails of the plurality of guide rails;
    a sled having opposed first and second body ends and having multiple opposed legs configured to partially capture there between the first and second guide rails, each of the legs positioned externally to and retained in sliding continuous contact with one of the first or second guide rails limiting sled motion to each of a loading direction and an ejection direction that are parallel to a sled longitudinal axis;

a member movably connected to the analysis device, the sled coupled to the member such that member movement in a first direction displaces the sled in the loading direction to position the sled in a test strip test position, and opposite member movement in a second direction operates to displace the sled in the ejection direction away from the test strip test position to eject the test strip from the analysis device by sled travel toward a test strip ejection position; and each of the legs having an inner shape selected to contact and partially capture an external face of one of the guide rails, thereby limiting displacement of the sled to only sliding motion in either the loading direction or the ejection direction;

wherein the multiple opposed legs includes at least first and second legs on a first side of the sled longitudinal axis and at least third and fourth legs on a second side of the sled longitudinal axis;

wherein the sled includes opposed first and second contact legs connected to the sled, the first contact leg being positioned on the first side of the sled longitudinal axis between the first and second legs and the second contact leg being positioned on the second side of the sled longitudinal axis between the third and fourth legs;

wherein the first and second contact legs are positioned within a rail cavity defined between the first and second guide rails, the test strip when positioned within rail cavity directly contacting the first and second contact legs.

* * * * *